US00PP30370P3

(12) United States Plant Patent

Klemm et al.

(10) Patent No.: US PP30,370 P3

(45) Date of Patent: Apr. 9, 2019

(54) *PELARGONIUM* PLANT NAMED 'KLEPP16390'

(50) Latin Name: *Pelargonium peltatum*
Varietal Denomination: KLEPP16390

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 43 days.

(21) Appl. No.: 15/731,357

(22) Filed: Jun. 1, 2017

(65) Prior Publication Data

US 2018/0352707 P1 Dec. 6, 2018

(51) Int. Cl.
*A01H 5/02* (2018.01)
*A01H 6/42* (2018.01)

(52) U.S. Cl.
USPC ..... Plt./332
CPC ..... *A01H 6/425* (2018.05)

(58) Field of Classification Search
USPC ..... Plt./332
CPC ..... A01H 5/02
See application file for complete search history.

*Primary Examiner* — Kent L Bell

(74) *Attorney, Agent, or Firm* — Bethany R. Roahrig; Cochran Freund & Young LLC

(57) ABSTRACT

A new *pelargonium* plant particularly distinguished by red and pink bi-colored flowers and a hanging growth habit, is disclosed.

1 Drawing Sheet

Genus and species: *Pelargonium peltatum.*
Variety denomination: 'KLEPP16390'.

BACKGROUND OF THE NEW PLANT

The present invention comprises a new and distinct variety of *pelargonium*, botanically known as *Pelargonium peltatum* and hereinafter referred to by the variety name 'KLEPP16390'. 'KLEPP16390' originated from a grafting in September 2012 in Stuttgart, Germany. The *pelargonium* variety 'Mexicanerin' (unpatented), which contains a unique viroid that causes dichroism, was used as the rootstock and the *pelargonium* variety 'Royal Scarlet XL' (unpatented) was the scion.

In November 2012, shoot tip cuttings were taken and propagated. The viroid of 'Mexicanerin' passed to the grafting and yielded a new phenotype of bi-colored red and pink flowers. A single plant was selected in September 2012 and subsequently named 'KLEPP16390'.

'KLEPP16390' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Red and pink bi-colored flowers; and
2. A hanging growth habit.

DESCRIPTION OF THE PHOTOGRAPH

This new *pelargonium* plant is illustrated by the accompanying photograph which shows an overall view of the plant. The photograph is of an approximately seven weeks old plant grown in Stuttgart, Germany under greenhouse conditions in April 2013. The colors shown are as true as can be reasonably obtained by conventional photographic procedures.

DESCRIPTION OF THE NEW VARIETY

The following detailed descriptions set forth the distinctive characteristics of 'KLEPP16390'. The data which define these characteristics were collected from asexual reproductions carried out in Stuttgart, Germany. Data was collected on plants grown four months after planting in Stuttgart, Germany under a glass covered greenhouse in May 2017. Color references are to The R.H.S. Colour Chart of The Royal Horticultural Society of London (R.H.S.), 5$^{th}$ edition (2007).

Classification:
- *Family.*—Geraniaceae.
- *Botanical.*—*Pelargonium peltatum.*
- *Common.*—*Pelargonium.*
- *Designation.*—'KLEPP16390'.

Parentage:
- *Rootstock.*—The *pelargonium* variety 'Mexicanerin' (unpatented).
- *Scion.*—The *pelargonium* variety 'Royal Scarlet XL' (unpatented).

Plant:
- *Form.*—Bushy and round.
- *Habit.*—Hanging.
- *Height.*—18.0 cm.
- *Spread.*—18.0 cm.
- *Natural flowering season.*—Spring to autumn.
- *Propagation type.*—Vegetative cuttings.
- *Time to produce a finished flowering plant.*—3 months.
- *Time to initiate and develop roots.*—21 days.
- *Root description.*—White and fine.

Stems:
*Quantity of stems per plant.*—4 to 5.
*Color.*—RHS 138A.
*Surface texture.*—Smooth.
*Stem form.*—Round.
*Diameter.*—0.6 cm.
*Length.*—8.0 cm to 10.0 cm.
*Internode length.*—2.0 cm to 5.0 cm.
*Anthocyanin.*—Absent.

Leaves:
*Arrangement.*—Alternate.
*Shape.*—Ivy-shaped.
*Apex.*—Obtuse.
*Base.*—Obtuse.
*Margin.*—Slightly crenate.
*Texture (both surfaces).*—Smooth.
*Length.*—6.0 cm to 7.0 cm.
*Width.*—7.0 cm.
*Color.*—Upper surface: RHS 137A and RHS N186C. Lower surface: RHS 137C.
*Petiole.*—Length: 4.0 cm to 6.0 cm. Diameter: 0.2 cm. Color: RHS 137C. Strength: Medium.
*Venation pattern.*—Palmate.
*Venation color.*—Upper surface: RHS 137B. Lower surface: RHS 137C.

Inflorescence:
*Lastingness of flowers on the plant.*—5 to 6 days.
*Umbels.*—Quantity of umbels per plant: 3 to 4. Length: 7.0 cm. Diameter: 7.0 cm.
*Individual florets of the umbel.*—Quantity of florets per umbel: 6 to 10. Depth: 2.0 cm. Diameter: 5.0 cm.
*Fragrance.*—Absent.

Flower buds:
*Cluster shape.*—Round.
*Cluster size.*—Length: 3.0 cm. Width: 3.0 cm.
*Surface texture.*—Moderately pubescent.
*Bud.*—Height: 1.5 cm. Width: 0.7 cm. Shape: Elliptic. Apex: Acute. Base: Obtuse. Margin: Entire. Color: RHS 138B.

Petals:
*Quantity per flower.*—10 to 12.
*Shape.*—Obtriangular.
*Apex.*—Round.
*Base.*—Obtuse.
*Margin.*—Entire.
*Length.*—2.2 cm.
*Width.*—1.8 cm.
*Texture (both surfaces).*—Smooth.
*Color of lobes.*—Upper lobes: Upper surface: RHS 42A and RHS 56B. Lower surface: RHS 41A and RHS 56B. Lower lobes: Upper surface: RHS 42A and RHS 56B. Lower surface: RHS 41A and RHS 56B.

Petaloids:
*Quantity per flower.*—1 to 5.
*Shape.*—Irregular.
*Apex.*—Round.
*Base.*—Obtuse.
*Margin.*—Entire.
*Length.*—1.8 cm.
*Width.*—1.0 cm.
*Texture (both surfaces).*—Smooth.
*Color.*—Upper surface: RHS 42A and RHS 56B. Lower surface: RHS 41A and RHS 56B.

Sepals:
*Number per flower.*—5.
*Shape.*—Elliptic.
*Apex.*—Acute.
*Base.*—Obtuse.
*Margin.*—Entire.
*Surface texture.*—Upper surface: Smooth. Lower surface: Moderately pubescent.
*Color.*—Upper surface: RHS 138B. Lower surface: RHS 138B.
*Length.*—1.8 cm.
*Width.*—0.6 cm.

Pedicel:
*Length.*—2.0 cm
*Diameter.*—0.15 cm.
*Color.*—RHS 177B.
*Surface texture.*—Sparsely pubescent.
*Strength.*—Medium.

Peduncle:
*Length.*—8.0 cm to 10.0 cm.
*Diameter.*—0.4 cm.
*Color.*—RHS 138B.
*Surface texture.*—Sparsely pubescent.
*Strength.*—Medium.

Reproductive organs:
*Stamens.*—Quantity of stamens per flower: 5. Anther length: 0.2 cm. Filament length: 0.5 cm. Filament color: RHS 69C. Pollen amount: Sparse. Pollen color: RHS 31B.
*Pistils.*—Number: 1. Stigma color: RHS 59C. Style length: 0.5 cm. Style color: RHS 62D. Ovary arrangement: Central. Ovary color: RHS 138D. Ovary diameter: 0.2 cm. Ovary length: 0.4 cm.

Fruit and seed set: None observed.
Disease and pest/insect resistance: None observed.

COMPARISON WITH PARENTAL LINES AND KNOWN VARIETY

'KLEPP16390' is distinguished from its parents as described in Table 1:

TABLE 1

Comparison with Parental Lines

| Characteristic | 'KLEPP16390' | Rootstock 'Mexicanerin' | Scion 'Royal Scarlet XL' |
|---|---|---|---|
| Growth | Medium | Strong | Strong |
| Flower color | Red and pink | Purple and white | Red |

'KLEPP16390' can be compared to the commercial variety ROYAL 'Candy Cane', also known as 'KLEP01028' (unpatented). Differences between the two varieties are described in Table 2:

TABLE 2

Comparison with Similar Variety

| Characteristic | 'KLEPP16390' | Commercial line ROYAL 'Candy Cane' |
|---|---|---|
| Earliness to flower | Early | Medium to late |
| Growth | Medium | Compact |

We claim:

1. A new and distinct variety of *pelargonium* plant named 'KLEPP16390' as illustrated and described herein.

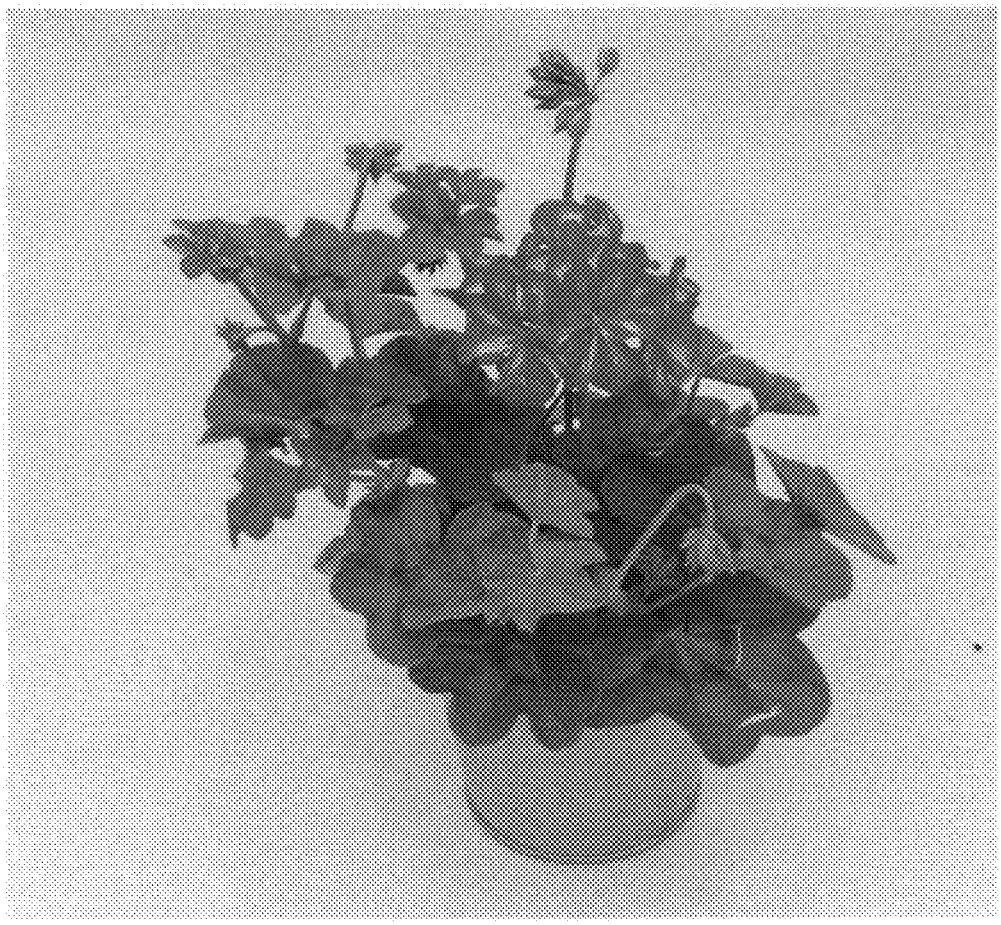

* * * * *